US012636052B2

(12) United States Patent　　(10) Patent No.:　US 12,636,052 B2

Menze et al.　　(45) Date of Patent:　May 26, 2026

(54) TIBIA AIMING JIG

(71) Applicant: DEPUY SYNTHES PRODUCTS, INC., Raynham, MA (US)

(72) Inventors: Johanna Menze, Zurich (CH); André Weber, Olten (CH); Martin Altmann, Zuchwil (CH); Andreas Baeriswyl, Büren an der Aare (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 146 days.

(21) Appl. No.: 18/352,209

(22) Filed: Jul. 13, 2023

(65) Prior Publication Data

US 2025/0017637 A1　　Jan. 16, 2025

(51) Int. Cl.
A61B 17/80　　(2006.01)
A61B 17/17　　(2006.01)

(52) U.S. Cl.
CPC ........ A61B 17/808 (2013.01); A61B 17/1764 (2013.01)

(58) Field of Classification Search
CPC .......................... A61B 17/808; A61B 17/1728
See application file for complete search history.

(56) References Cited

U.S. PATENT DOCUMENTS

| | | | |
|---|---|---|---|
| 7,462,199 B2 | 12/2008 | Justin | |
| 7,588,577 B2 * | 9/2009 | Fencl | A61B 17/72 |
| | | | 606/62 |
| 10,368,928 B2 | 8/2019 | Lueth | |

| | | | |
|---|---|---|---|
| 11,096,730 B2 | 8/2021 | Tiongson | |
| 2020/0015868 A1 | 1/2020 | Dacosta | |
| 2022/0000496 A1 | 1/2022 | Dacosta | |

FOREIGN PATENT DOCUMENTS

| | | |
|---|---|---|
| AU | 2014205267 A1 | 7/2015 |
| CN | 202235652 | 5/2012 |
| CN | 106264697 A | 1/2017 |
| CN | 206566008 | 10/2017 |
| CN | 211066977 | 7/2020 |
| CN | 216535472 | 5/2022 |
| CN | 115645023 A | 1/2023 |
| JP | 5283956 | 9/2013 |
| KR | 20230105363 A | 7/2023 |
| WO | 2022173776 A1 | 8/2022 |

OTHER PUBLICATIONS

International Search Report and Written Opinion for corresponding International Application No. PCT/IB2024/056764 mailed on Oct. 9, 2024.

* cited by examiner

*Primary Examiner* — Andrew Yang

(74) *Attorney, Agent, or Firm* — Kramer & Amado, P.C.

(57)　　　ABSTRACT

An aiming jig for a tibia plate, including: a head the interfaces with a head of the tibia plate comprising: screw guide holes corresponding to screw holes in the head of the tibia plate; a fixation protrusion that engages a fixation opening in the head of the tibia plate, wherein an engagement of the fixation protrusion with the fixation opening aligns the head with the head of the tibia plate; and an arm extending from the head including a guide wherein the guide is configured to extend along an anterior portion of a tibia when the aiming jig is fixed to the tibia plate, and the guide includes a support screw guide hole that guides a placement of a support screw into the tibia in a generally anterior to posterior direction so that the support screw avoids interfering with plate screws placed in the head of the tibia plate.

21 Claims, 11 Drawing Sheets

200

204

202

200

204

202

TIBIA AIMING JIG

FIELD OF THE DISCLOSURE

Various exemplary embodiments disclosed herein relate to a tibia aiming jig, specifically a proximal tibia aiming jig for anteroposterior screw insertion above lateral plate rafting screws.

BACKGROUND

Tibia plates have been developed for addressing fractures in the tibia including fractures of the proximal tibia. A lateral proximal tibia plate may include a head and a body. The body may extend along the tibia and includes screw holes so that the tibia plate may be attached to the tibia. The head may include a row of screw holes at the end of the tibia plate. When screws are placed in these holes they may be used to capture, reduce, and secure fractured bone fragments. This row of screws may be called rafting screws as they provide a raft of support for the articular surface of the fractured tibia. In the clinical routine for addressing fractures of the proximal tibia, isolated screws are often placed from the anterior to the posterior, just above and very close to the most proximal rafting screw row of the lateral proximal tibia plate. These screws may be called support screws. The intention of the support screws is to provide additional stability to the articular surface which is often comminuted or fractured in multiple small fragments. Additionally, the support screws allow for fixation of the posterolateral fracture fragments which remain a clinical challenge. Further, these support screws may provide support for the articular surface (as they are closer to the articular surface) when the plate and the rafting screws are more distant from the articular surface. Also there is a posterior corner of the tibia adjacent the fibular head that is difficult to reach with the lateral proximal tibia plate, so these support screws may reach this area and provide support for the tibia and may capture, reduce, and secure other bone fragments when repairing the fracture.

SUMMARY

A summary of various exemplary embodiments is presented below.

Various embodiments relate to an aiming jig for a tibia plate, including: a head configured to interface with a head of the tibia plate including: a plurality of screw guide holes corresponding to a plurality of screw holes in the head of the tibia plate; a fixation protrusion configured to engage a fixation opening in the head of the tibia plate, wherein an engagement of the fixation protrusion with the fixation opening aligns the head with the head of the tibia plate; and an arm extending from the head including a guide wherein the guide is configured to extend along an anterior portion of a tibia when the aiming jig is fixed to the tibia plate, and the guide includes a support screw guide hole configured to guide a placement of a support screw into the tibia in a generally anterior to posterior direction so that the support screw avoids interfering with plate screws placed in the head of the tibia plate.

Various embodiments are described, wherein the head further includes a plurality of guide holes corresponding to a plurality of plate guide holes in the tibia plate.

Various embodiments are described, wherein the arm is configured so that the guide avoids contact with a patient when the aiming jig is fixed to the tibia plate.

Various embodiments are described, wherein the guide includes a plurality of guide holes.

Various embodiments are described, further including a sleeve configured to be inserted in the support screw guide hole and to come into contact with an anterior surface of the tibia.

Various embodiments are described, further including a retention pin configured to be inserted into a retention opening in the guide wherein the retention pin retains the sleeve and fixes the sleeve to the guide.

Various embodiments are described, wherein the support screw guide hole has a location and orientation so that the support screw is placed between the plate screws and an articular surface of the tibia.

Various embodiments are described, wherein the support screw guide hole has a location and orientation so that the support screw is placed so that a portion of the plate screws are between the support screw and an articular surface of the tibia.

Various embodiments are described, wherein an end of the support screw is within the tibia.

Various embodiments are described, wherein the head includes a fixation screw hole, and the aiming jig includes a fixation screw configured to engage a fixation opening in the tibia plate via the fixation screw hole.

Various embodiments are described, wherein the head includes a body with a first portion of the plurality of screw guide holes configured to guide a first portion of the plate screws placed in the head of the tibia plate to support an articular surface of the tibia.

Various embodiments are described, wherein the head includes a flange extending from the body with a second portion of the plurality of screw guide holes configured to guide a second portion of the plate screws placed in the head of the tibia plate, and wherein the flange includes a fixation screw hole configured to receive a fixation screw wherein the fixation screw is configured to engage a fixation opening in the tibia plate via the fixation screw hole.

Further various embodiments relate to a method for placing support screws into an anterior surface of a tibia using an aiming jig for a tibia plate, including: placing and aligning the tibia plate on the tibia; initially fixing the tibia plate to the tibia; placing the aiming jig onto the tibia plate; and placing a support screw in a generally anterior to posterior direction of the tibia using a guide on the aiming jig so that the support screw avoids interfering with plate screws placed in a head of the tibia plate.

Various embodiments are described, wherein initially fixing the tibia plate to the tibia includes placing plate screws in the tibia plate using guide holes in the aiming jig.

Various embodiments are described, wherein initially fixing the tibia plate to the tibia includes placing K-wires into the tibia through a guide hole in the aiming jig and a plate fixation hole in the tibia plate.

Various embodiments are described, wherein placing and aligning the tibia plate on the tibia includes placing a fixation protrusion on the aiming jig into a fixation opening in the tibia plate.

Various embodiments are described, wherein placing a support screw includes: drilling a hole in an anterior surface of the tibia using the guide; and driving the support screw into the drilled hole using the guide.

Various embodiments are described, wherein drilling the hole includes using a first sleeve in the guide, and driving the support screw includes using a second sleeve in the guide.

Various embodiments are described, further including retaining the first sleeve by the guide using a retention pin in the guide.

Various embodiments are described, wherein placing a support screw includes cutting a minimally invasive surgery incision through soft tissue to expose a cortex of an anterior surface of the tibia.

Various embodiments are described, wherein the aiming jig includes: a head configured interface with a head of the tibia plate including: a plurality of screw guide holes corresponding to a plurality of screw holes in the head of the tibia plate; a fixation protrusion configured to engage a fixation opening in the head of the tibia plate, wherein an engagement of the fixation protrusion with the fixation opening aligns the head with the head of the tibia plate; and an arm extending from the head including a guide wherein the guide extends along an anterior portion of the tibia when the aiming jig is fixed to the tibia plate, and the guide includes a support screw guide hole configured to guide a placement of a support screw into the tibia in a generally anterior to posterior direction so that the support screw avoids interfering with plate screws placed in the head of the tibia plate.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF DRAWINGS

So that the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

Figures 1A, 1B:
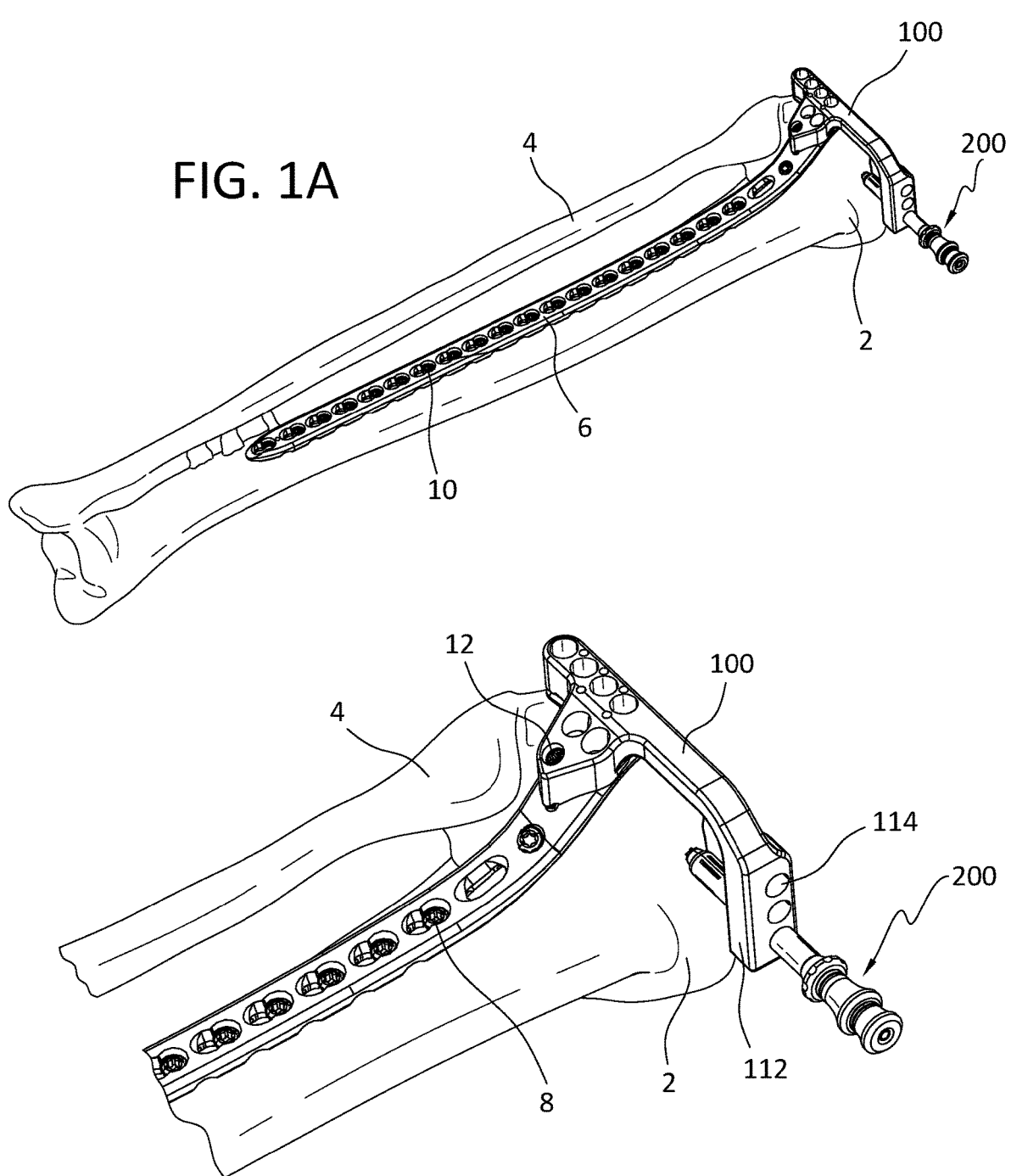
FIGS. 1A-D illustrate the application of a aiming jig to a tibia.
Figure 1C:
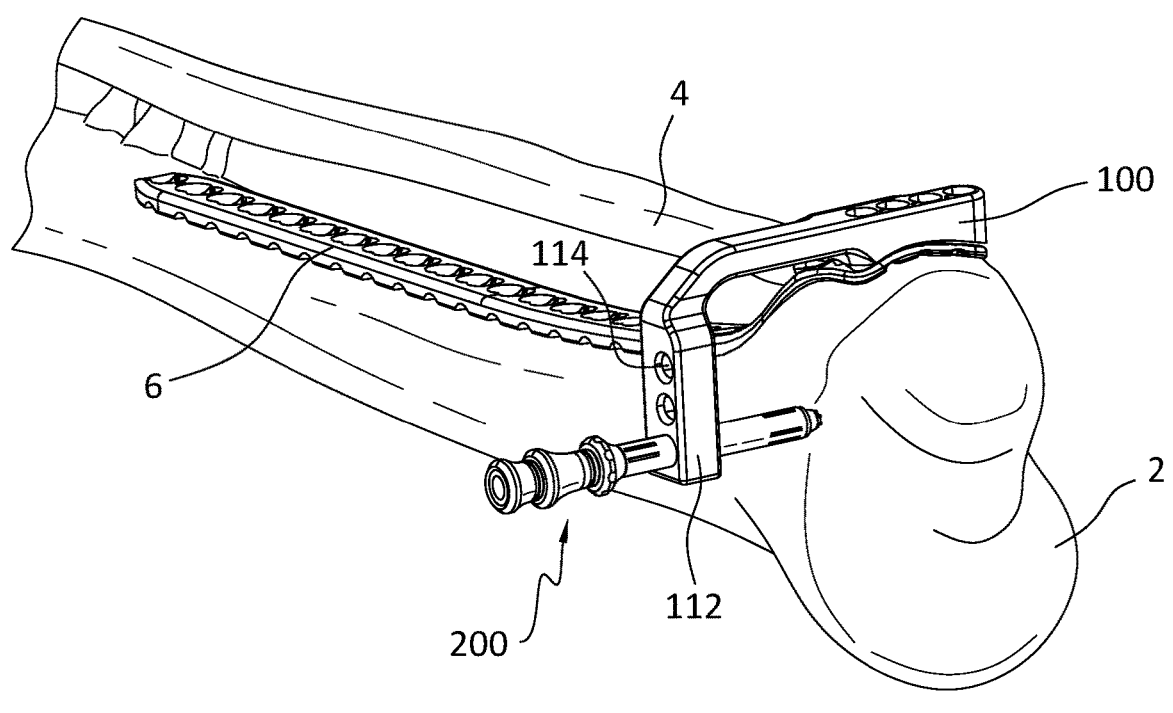
Figure 1D:
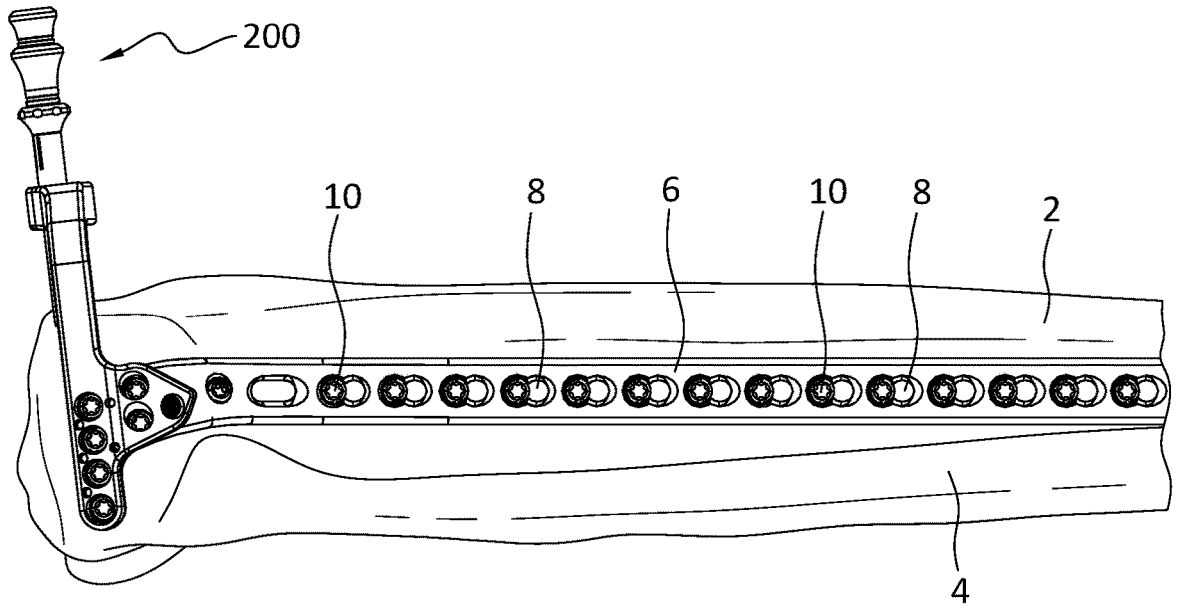

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Several aspects of bone plate jig systems will now be presented with reference to various apparatuses and techniques. These apparatuses and techniques will be described in the following detailed description and illustrated in the accompanying drawings by various blocks, modules, components, steps, processes, methods, and/or the like (collectively referred to as "elements").

Tibia plates have been developed for addressing fractures in the tibia including fractures of the proximal tibia. A lateral proximal tibia plate may include a head and a body. The body may extend along the tibia and includes screw holes so that the tibia plate may be attached to the tibia. The head may include a row of screw holes at the end of the tibia plate. When screws are placed in these holes they may be used to capture, reduce, and secure fractured bone fragments. This row of screws may be called rafting screws as they provide a raft of support for the articular surface of the fractured tibia. In the clinical routine for addressing fractures of the proximal tibia, isolated screws are often placed from anterior to posterior, just above and very close to the most proximal rafting screw row of the lateral proximal tibia plate. These screws may be called support screws. The intention of the support screws is to provide additional stability to the articular surface which is often comminuted or fractured in multiple small fragments. Additionally, the support screws allow for fixation of the posterolateral fracture fragments which remain a clinical challenge. Across the tibia plate, screws may be placed in any of the holes to meet specific clinical requirements of the patient.

Currently, surgeons position the support screws frechand because no guidance or helping devices are available. However, it is crucial to place the support screws as close as possible to the lateral rafting screws as these provide the resistance against subsidence which needs to be avoided for the tibia plateau by any means. Consequently, the support screws are currently placed with the help of extensive imaging which leads to high radiation exposure. Additionally, surgeons often hit the lateral rafting screws while drilling for the anterior-posterior screw hole. This could lead to damage and later failure of those screws or breakage of the drill bit, which results in the hassle of removing the broken drill bit tip from the body.

An aiming jig is disclosed herein to assist in the placement of the support screws. The aiming jig may act as a guide block to aid in the placement of screws in the tibia plate. The aiming jig additionally includes an extension arm to the anterior side of the tibia that guides the insertion of those support screws above the lateral rafting screws in a generally anterior to posterior direction. The aiming jig is placed on a lateral proximal tibia plate. The aiming jig and the tibia plate include an interface to ensure precise positioning of the jig. Fixation of the aiming jig to the tibia plate is accomplished, e.g., by a screw interface that engages a threaded hole in the tibia plate that is dedicated for the aiming jig or a regular guide block on the plate. The part of the aiming jig that is on the tibia plate has a similar shape and functionality as the regular guide block and therefore also allows for guided nominal screw insertion for the proximal plate holes (together with, e.g., a triple sleeve system as used with other systems). The extension arm is intended to remain above the soft tissue. It may include three holes in which the triple sleeve system may be inserted. Those sleeves will be pushed through the arm and through the soft tissue (possibly with previous small incisions) onto the bone. The triple sleeves provide the option to insert a K-wire, drill a pilot hole, and insert the screws. The outer sleeve additionally allows for screw hole depth measurements with the existing depth probe from other systems. In another embodiment, a depth probe may be slid over the K-wire to measure hole depth. Also the depth may be measured using a calibrated drill bit. In some embodiments, the holes in the extension arm may include a retention mechanism that prevents the sleeves from sliding out. The distance between the extension arm to the anterior proximal tibia cortex may be optimized to minimize soft tissue interference in a minimal invasive, percutaneous application while ensuring that sleeves always reach the anterior cortex, despite the variation of tibia morphology among subjects.

FIGS. 1A-D illustrate the application of an aiming jig 100 to a tibia 2. A fibula 4 is also illustrated along with the tibia 2. A tibia plate 6 is attached to the tibia 2 using plate screws 8 through plate screw holes 10 in the tibia plate 6. The aiming jig 100 is placed over a head of the tibia plate 6 and is properly aligned to the tibia plate 6 through the interface of the aiming jig 100 and the tibia plate 6. A fixation screw 12 is placed through a fixation screw hole 116 (see FIG. 3) to engage a plate fixation hole 14 in the tibia plate 6. As discussed above, a triple sleeve system 200 may be placed in guide hole 114 of a guide 112 on the aiming jig 100.

Figure 2A:
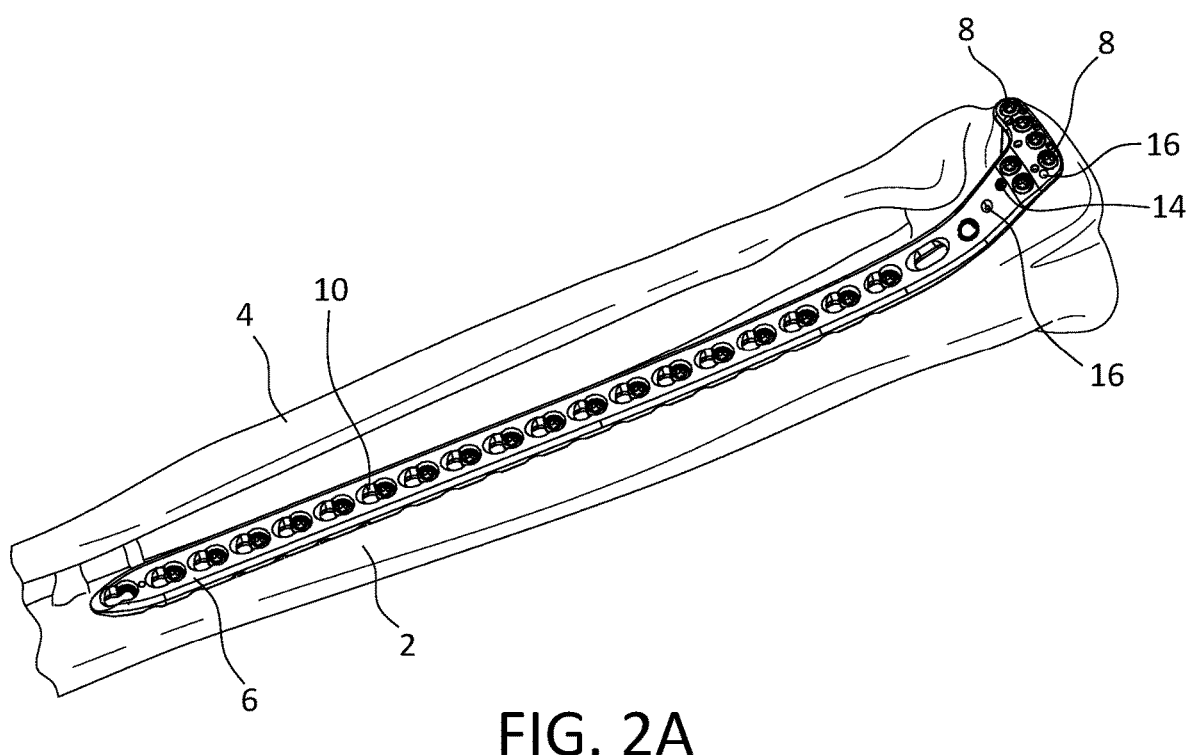
FIGS. 2A-B illustrate the tibia plate mounted on the tibia.
Figure 2B:
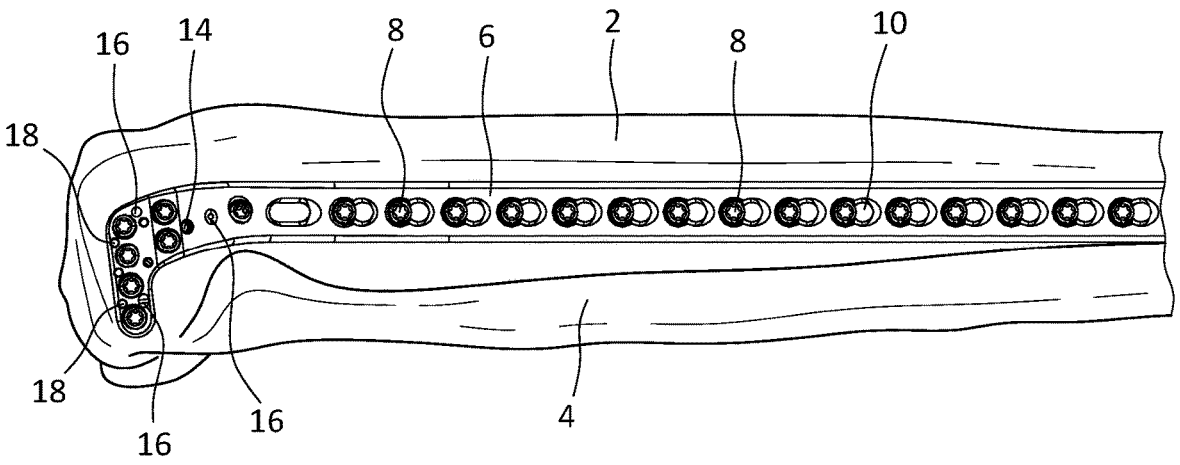

FIGS. 2A-B illustrate the tibia plate 6 mounted on the tibia 2. The tibia plate 6 has a body that is fixed to the length of the tibia 2 using plate screws 8 placed into the tibia 2 through plate screw holes 10. The plate screw hole 10 may be a combination hole that includes a threaded portion and a non-threaded portion. The threaded portion may be used with screws with threaded heads. Further, the plate screw holes 10 allow for the screws to be placed at various angles. The non-threaded hole portion allows for plate compression to the bone with screws also being able to be placed at various angles. Further, the tibia plate 6 includes a head with a variety of plate screw holes 10. The head of the tibia plate 6 is shaped to follow the contours of the tibial condyle. At the end of the head of the tibia plate 6 there are, for example, four plate screw holes 10 near the tibia articular surface to provide support to the tibia articular surface. These four plate screw holes 10 may accept the rafting screws. The tibia plate 6 may also have plate guide holes 18. The plate guide holes 18 may be used to place K-wires into the bone during the placement of the tibia plate 6.

The tibia plate 6 may also include a plate fixation hole 14 that is threaded. The fixation screw 12 may be placed through a fixation screw hole 116 in the aiming jig 100 to engage the plate fixation hole 14 to fix the aiming jig 100 to the tibia plate 6. The tibia plate 6 also includes fixation openings 16 that accept fixation protrusions 120 on the aiming jig 100. The fixation opening 16 and fixation protrusion 120 create an alignment interface that ensures that the aiming jig 100 is properly aligned to the tibia plate 6 when placed on the tibia plate 6. While the tibia plate 6 is shown with specific numbers and locations of the plate screw holes 10, fixation opening 16, and plate guide holes 18, other number and locations of these elements may also be used. In another embodiment, the fixation protrusion 120 may be a single fixation protrusion 120 with a specific shape (e.g., a triangle, star, cross, etc.) that engages the fixation opening 16 where the fixation openings 16 has a complementary shape that guides the aiming jig 100 into the proper orientation relative to the tibia plate 6. In this case, only a single fixation protrusion 120 and fixation opening 16 may be used. Further, the specific shape of the tibia plate 6 may also take on other shapes as well. In another embodiment, the fixation protrusion 120 and the fixation opening 16 may be swapped, i.e., the tibia plate 6 may have a fixation protrusion, and the aiming jig 100 may have fixation opening. Accordingly, the interface between the tibia plate 6 and the aiming jig 100 may generically be described as having first interface elements and second interface elements, where the first and second interface elements interact to align the tibia plate 6 and the aiming jig 100. The first and second interface elements are complementary and may include fixation protrusions and fixation openings.

Figure 3:
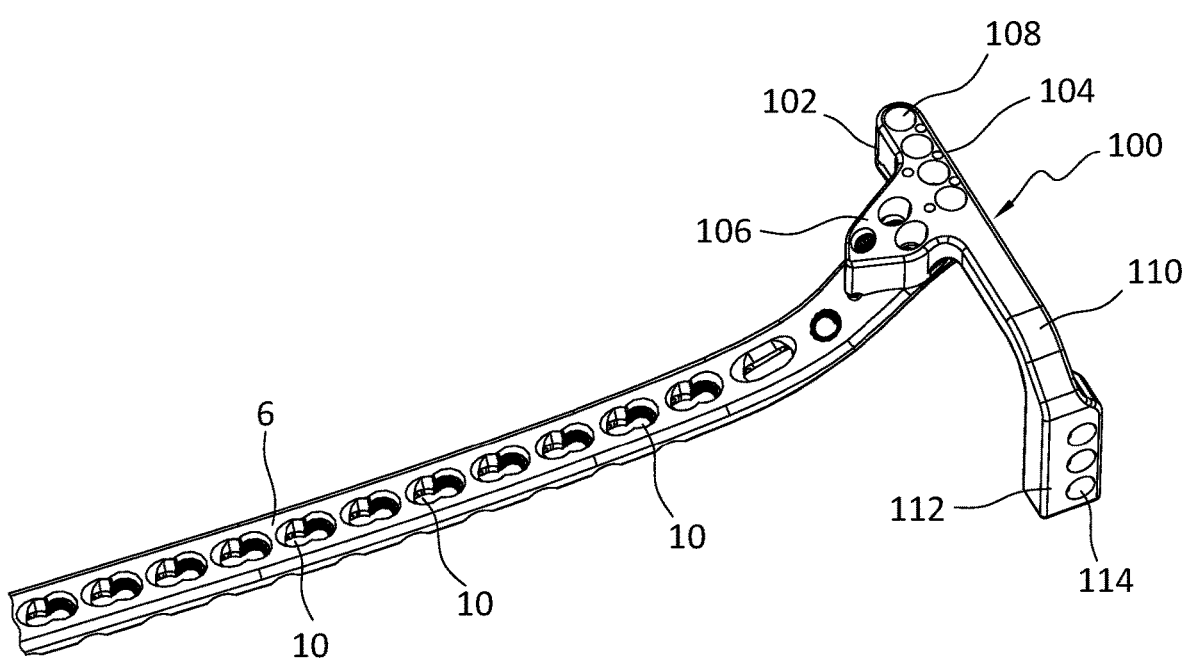
FIG. 3 illustrates the aiming jig engaged with the tibia plate.

FIG. 3 illustrates the aiming jig 100 engaged with the tibia plate 6. When the aiming jig 100 engages the tibia plate 6, the fixation protrusions 120 engage the fixation openings 16 to align the aiming jig 100 to the tibia plate 6. Further, the screw guide holes 108 and K-wire guide holes 118 in the aiming jig 100 align with the plate screw holes 10 and plate guide holes 18, respectively. The aiming jig 100 may be fixed to the tibia plate 6 by inserting fixation screw 12 through the fixation screw hole 116 to engage the plate fixation hole 14. The screw guide holes 108 may be used to assist in guiding the placement of plate screws 8 in the tibia plate 6. The screw guide holes 108 may guide a drill in the proper orientation for the placement of the plate screws 8 in the plate screw holes 10 of the tibia plate 6. The screw guide holes 108 may interface with a drill guide used to guide the drill during drilling. For example, outer sleeve 202 may be used as a drill guide. The location and orientation of the screw guide holes 108 are carefully chosen so that the plate screws 8 that act as the raft screws are in a precise known location so that the support screws can later be placed near the raft screws while avoiding interfering with the raft screws. Further, these support screws do not extend through and exit the tibia.

Figure 4A:
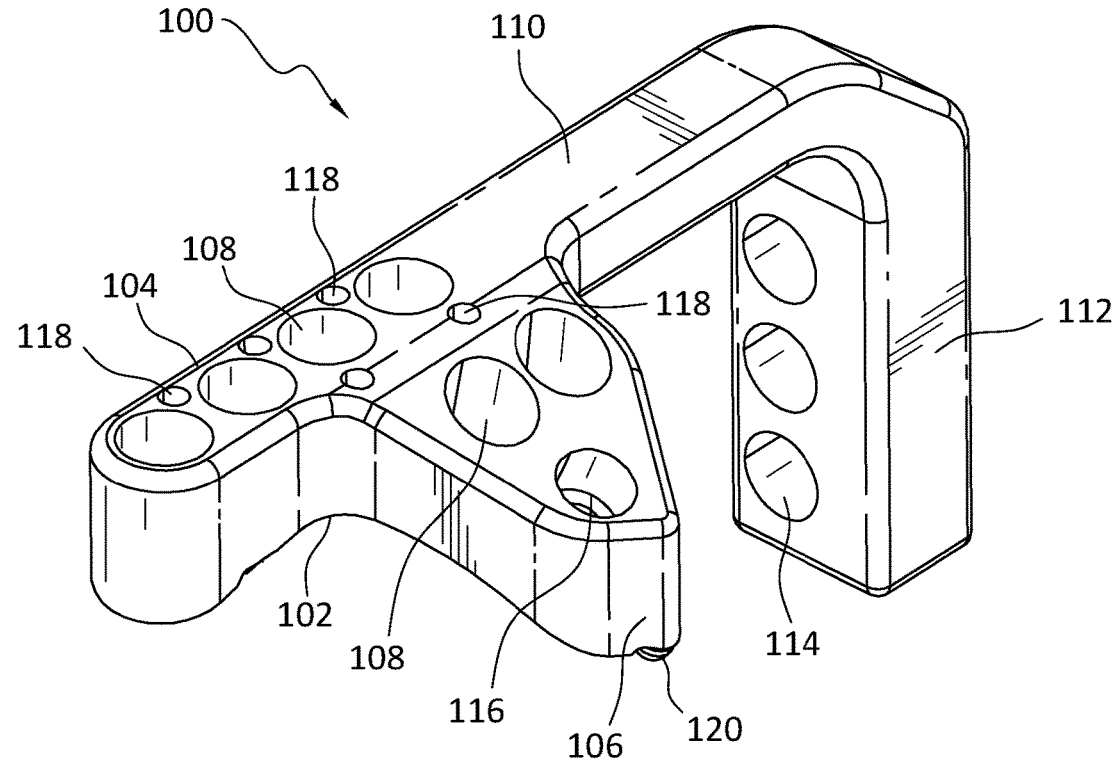
FIGS. 4A-B illustrate top perspective views of the aiming jig.
Figure 4B:
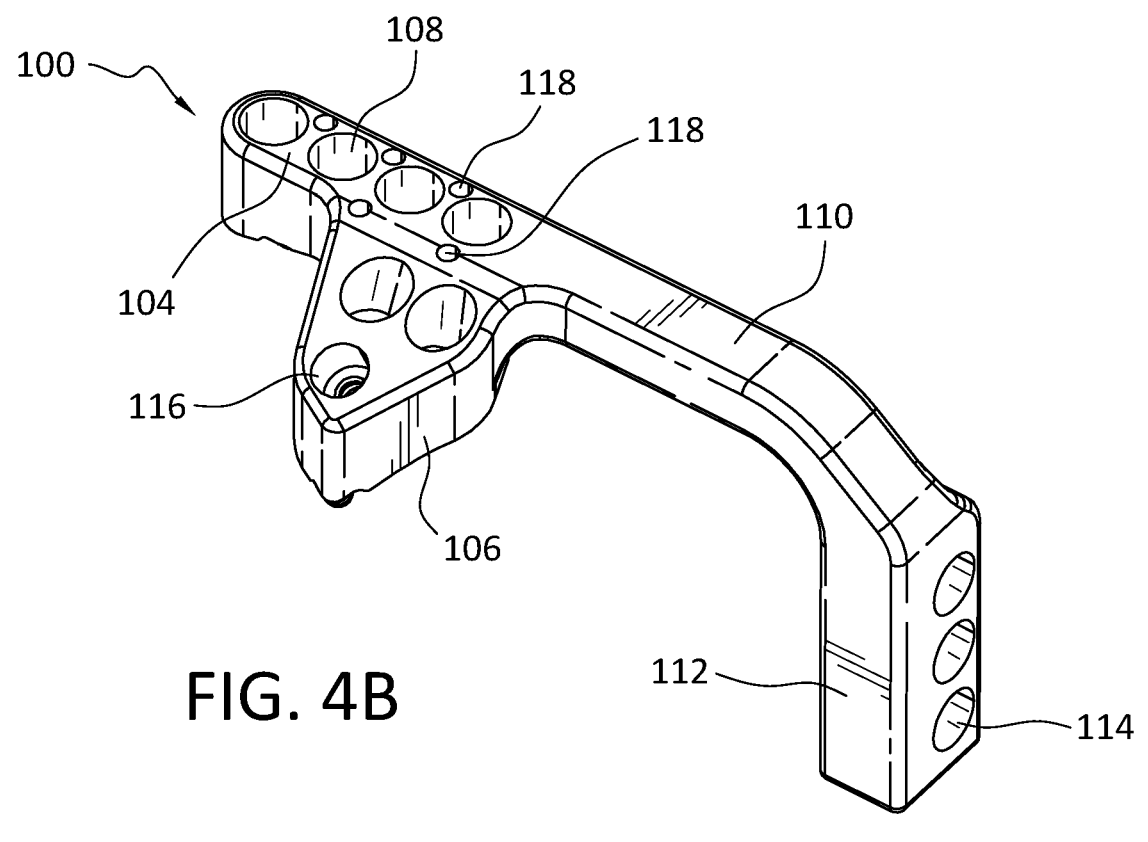
Figure 4C:
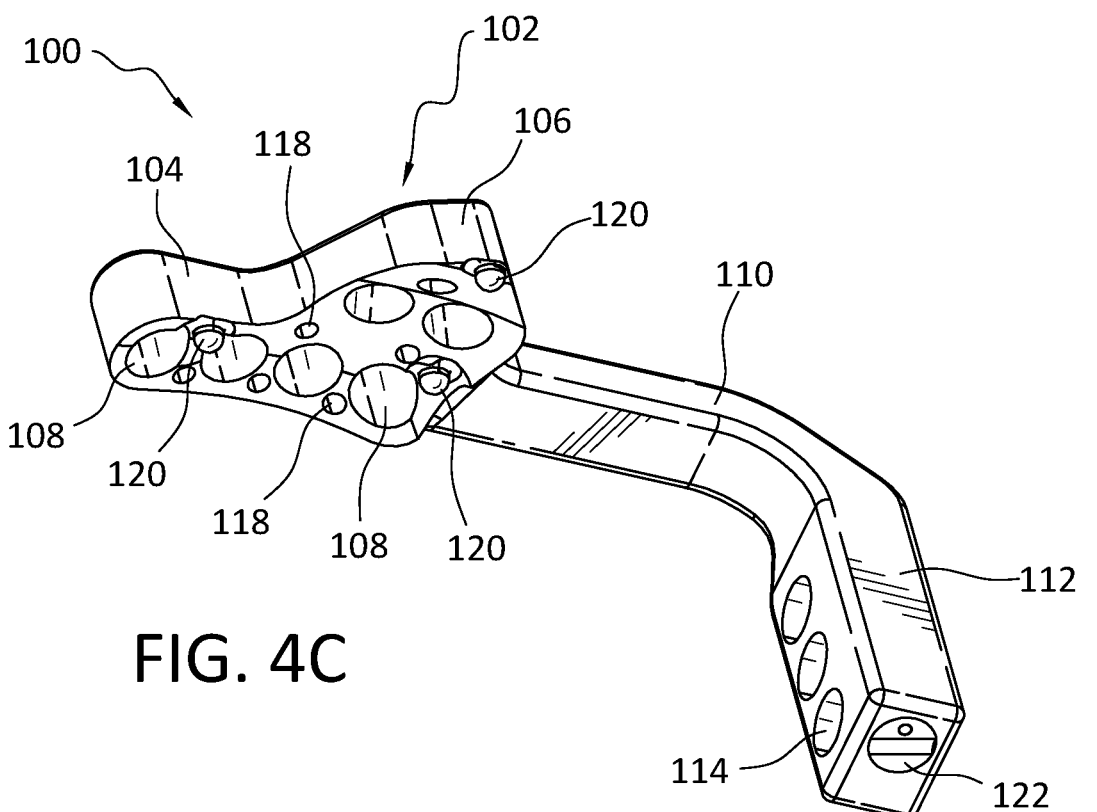
FIG. 4C illustrates a bottom perspective view of the aiming jig.
Figures 4D, 4E, 4F:
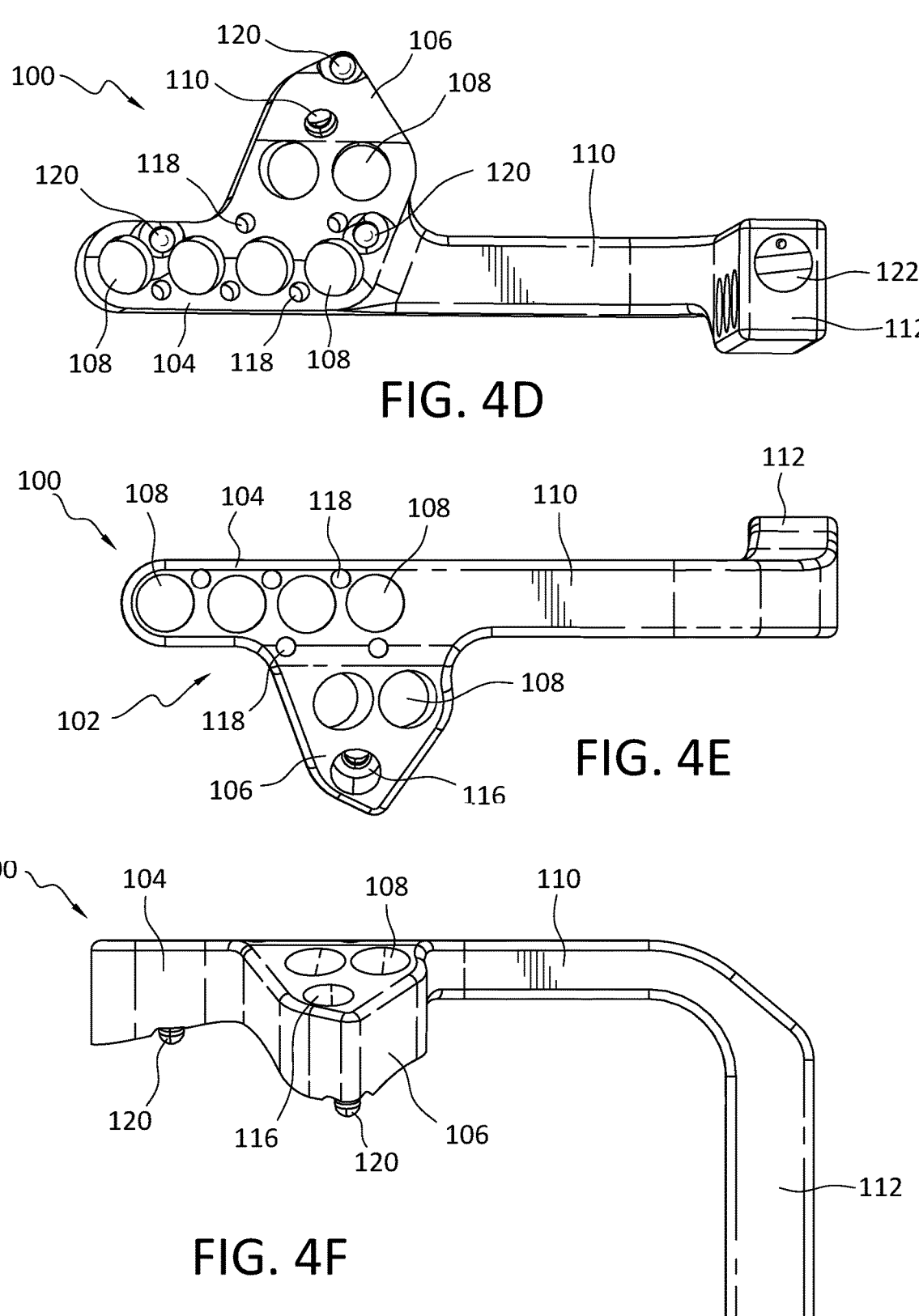
FIGS. 4D-F illustrated bottom, top, and side views of the aiming jig.
Figures 4G, 4H:
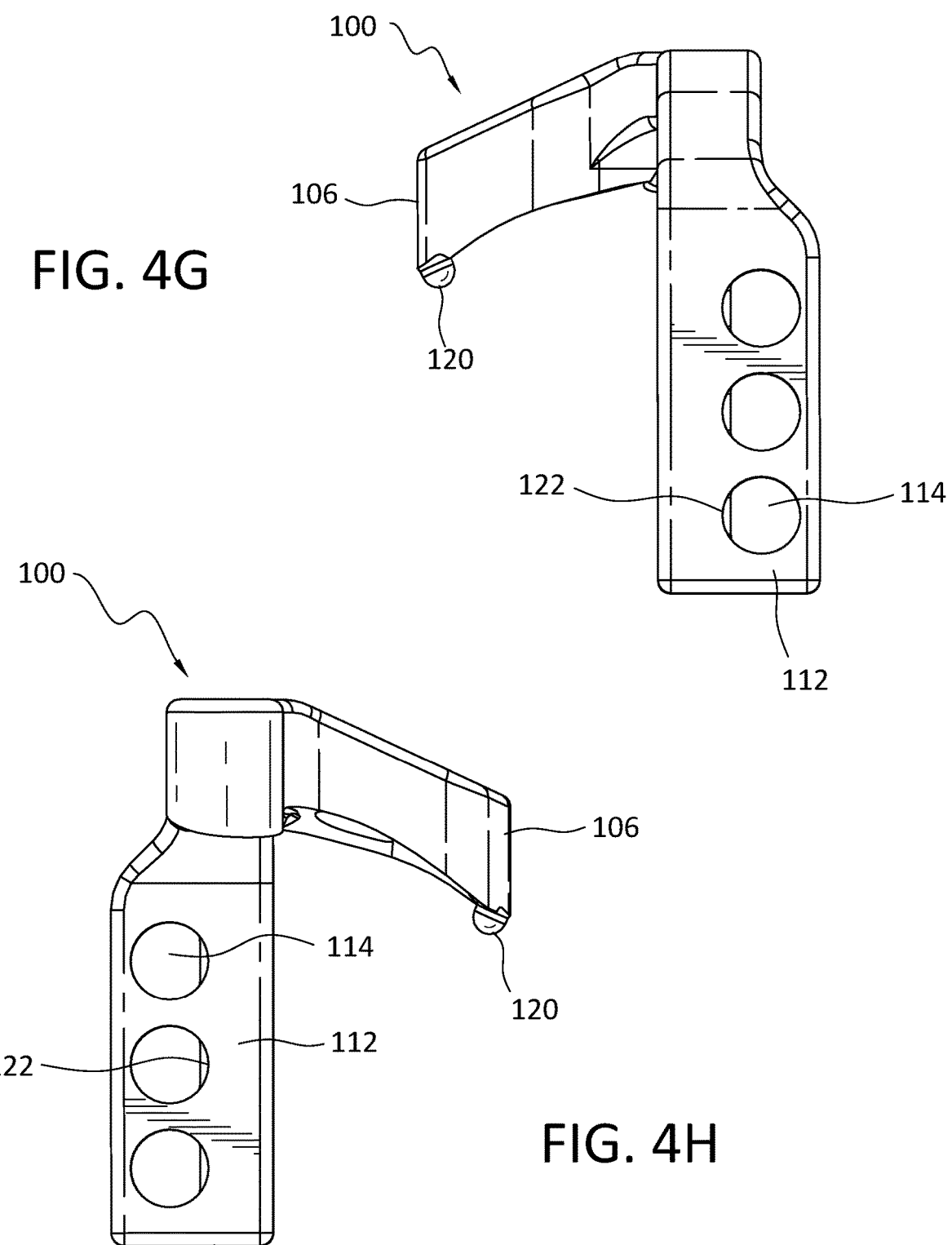
FIGS. 4G-H illustrate two end views of the aiming jig.

FIGS. 4A-B illustrate top perspective views of the aiming jig 100. FIG. 4C illustrates a bottom perspective view of the aiming jig 100. FIGS. 4D-F illustrated bottom, top, and side views of the aiming jig 100. FIGS. G-H illustrate two end views of the aiming jig 100. The aiming jig 100 includes a head 102 and arm 110.

The head 102 may have a shape that generally corresponds to the shape of the head of the tibia plate 6. The head 102 may include a body 104 and a flange 106. In this example, the body is a generally strait structure with four screw guide holes 108 and three K-wire guide holes 118. Other numbers of screw guide holes 108 and K-wire guide holes 118 may also be used in the body 104. The flange 106 may extend from the body 104 and in this example includes two K-wire guide holes 118, two screw guide holes 108, and a fixation screw hole 116. Other numbers of K-wire guide holes 118 and screw guide holes 108 may also be used in the flange 106. The K-wire guide holes 118, screw guide holes 108, and fixation screw hole 116 of the head 102 align with plate guide holes 18, plate screw holes 10, and plate fixation hole 14 respectively. The underside of the head 102 may include fixation protrusions 120 (i.e., first interface elements). The location of fixation protrusions 120 correspond to the locations of the fixation openings 16 (i.e., second interface elements) in the tibia plate 6. Three fixation protrusions 120 are illustrated, but other numbers of fixation protrusions 120 may be used as well. In alternative embodiment, two or more of the K-wire guide holes 118 may be used to align the aiming jig 100 to the tibia plate 6. This may be done by driving K-wires into the tibia 2 through the plate guide hole 18. Then aiming jig 100 may be slid onto the K-wires using the K-wire guide holes 118 corresponding to the location of the K-wires to then engage the tibia plate 6. Once the aiming jig 100 engages the tibia plate 6, a fixation screw 12 may engage the fixation opening 16 of the tibia plate 6 to fix the aiming jig 100 to the tibia plate 6. The fixation screw 12 may be a part of the aiming jig 100, where the aiming jig 100 captures the fixation screw 12. This means that the fixation screw 12 is always readily available to attach the aiming jig 100 to the tibia plate 6. In an alternative embodiment, a fixation screw 12 may be placed through the fixation screw hole 116 into the fixation opening 16 of the tibia plate 6 to fix the aiming jig 100 to the tibia plate 6. In this case the fixation screw 12 is separate from the aiming jig 100.

The arm 110 extends from the head 102 and includes the guide 112. The location, shape, and length of the arm 110 is selected so that the guide 112 clears the soft tissue of the patient, allows the instruments to reach the tibia, and properly aligns support screws placed into the patient. It is noted that in some applications the support screws may be placed above the raft screws, i.e., closer to the articular surface, but in other applications, the support screws may be placed below the raft screws, i.e., the raft screws are between the articular surface and the support screws. Accordingly, the shape and dimensions of the arm 110 and the guide 112 are selected to allow for the placement of the support screws in the desired location.

The guide 112 extends in a direction that runs along the side of the anterior proximal tibia when the aiming jig 100 is fixed to the tibia plate 6. In this example, the guide 112 includes three guide holes 114, but other numbers of guide holes 114 may be used in the guide 112. The location and axis of the guide holes 114 are selected so that support screws may be placed into the anterior proximal tibia in a generally anterior to posterior direction and in a way that does not interfere with the raft screws placed through the tibia plate 6. The triple sleeve system 200 may be used with the guide holes 114 to allow for the placement of K-wires, drilling, and the placement of screws into the anterior proximal tibia cortex. The guide holes 114 in the guide 112 are shown as having parallel central axes, but in other embodiments the direction of the one or more of the central axes of the guide holes 114 may be different. It is noted that the angle between the head 102 and the arm 110 determines the direction of the axes of the guide holes 114 and is also selected to achieve the desired angles for the support screws.

Figures 5A, 5B, 5C:
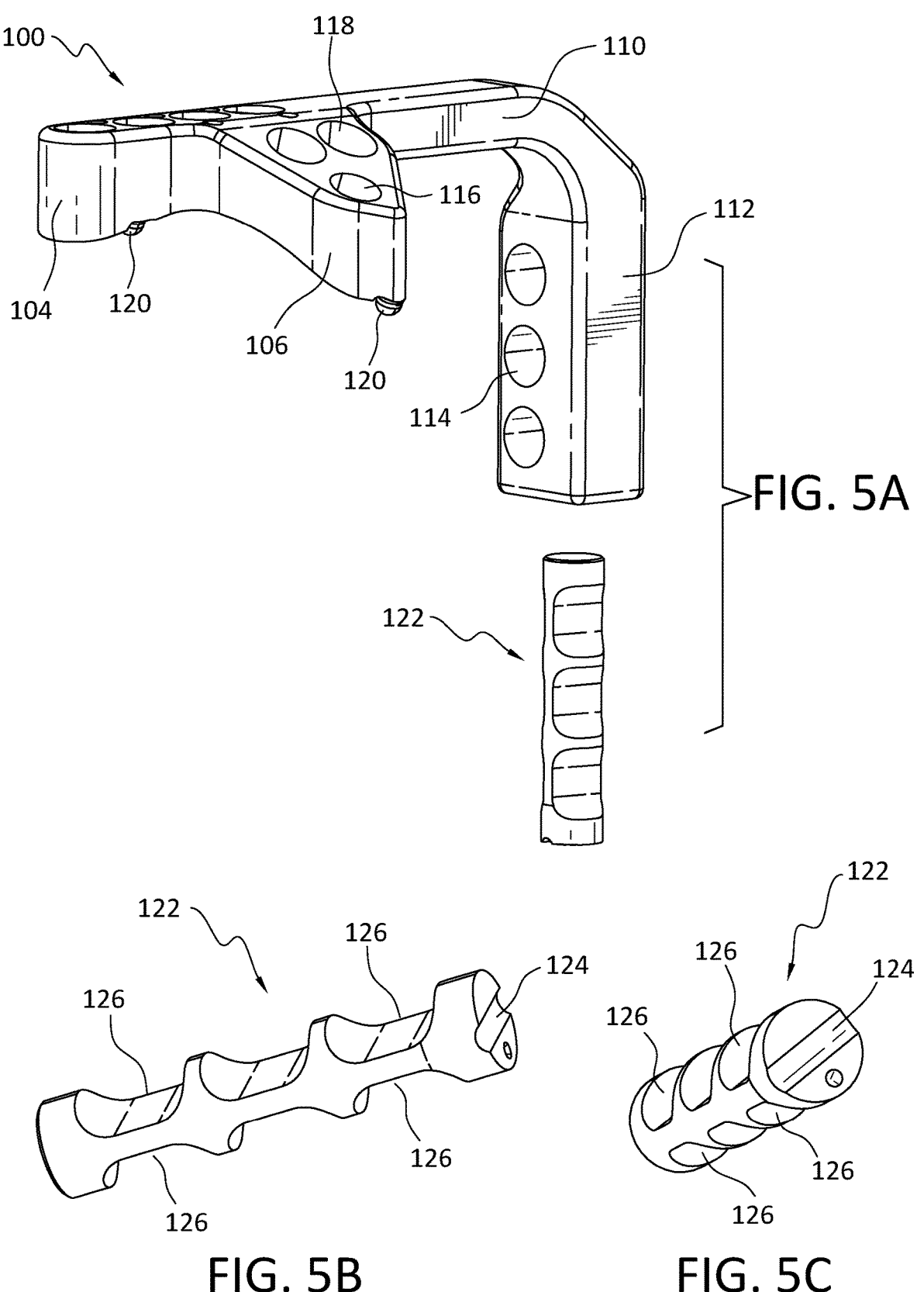
FIG. 5A illustrates the aiming jig and the retention pin.
FIG. 5B-C illustrate perspective views of the retention pin.

FIG. 5A illustrates the aiming jig 100 and the retention pin 122. FIG. 5B-C illustrate perspective views of the retention pin 122. The retention pin 122 helps to secure the triple sleeve system 200 in the guide 112 of the aiming jig 100. The retention pin 122 is placed in a retention hole that runs along the length of the retention pin 122 that partially intersects the guide holes 114. The retention pin 122 includes grooves 126. The grooves 126 correspond to the guide holes 114. The retention pin 122 also includes a slot 124 that may be used for assembly. Once the triple sleeve system 200 has been inserted through the guide hole 114, retention pin 122 may deform and engage the triple sleeve system 200. The retention pin 122 acts like a spring to cause the grooves 126 to engage the triple sleeve system 200 and to secure it to the guide 112.

Figure 6A:
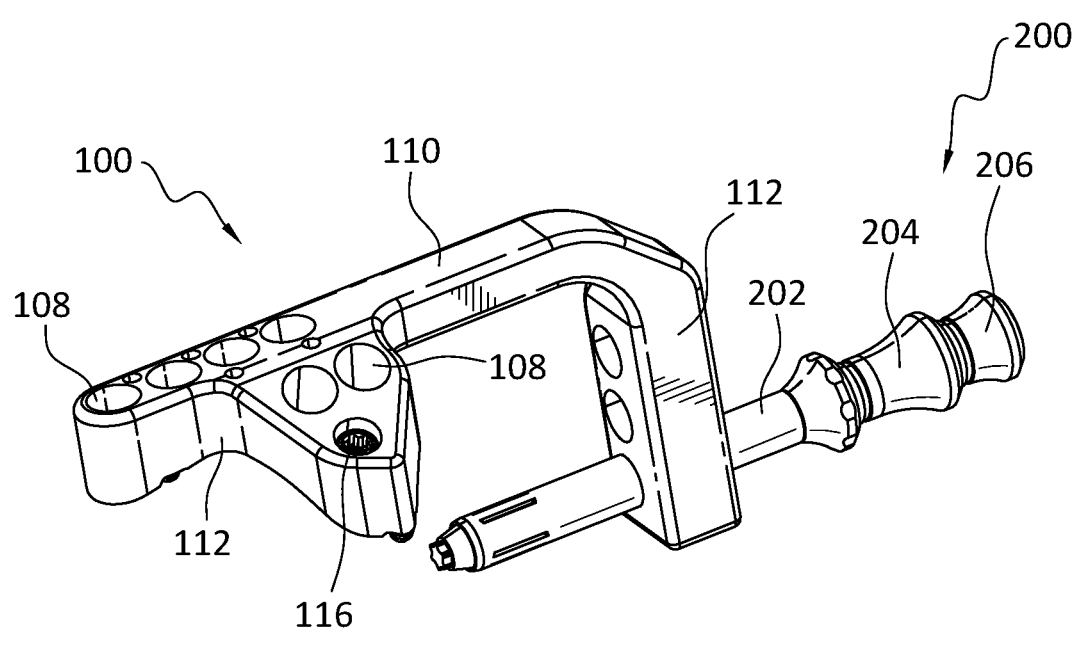
FIGS. 6A-B illustrate a triple sleeve system inserted through one of the guide holes of the aiming jig.
Figure 6B:
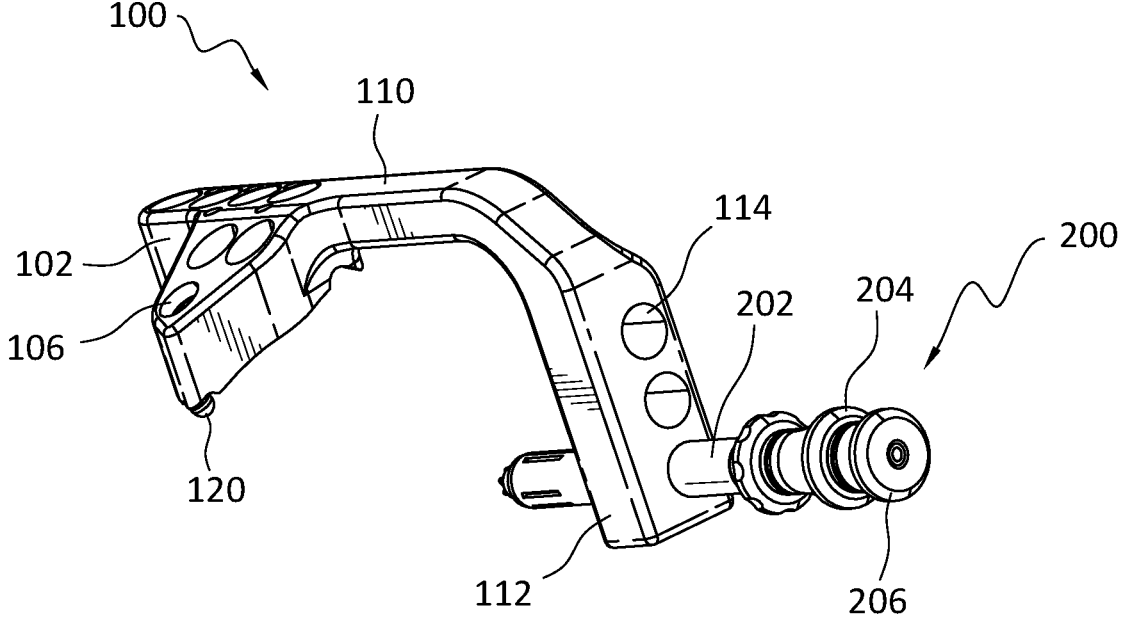

FIGS. 6A-B illustrate a triple sleeve system 200 inserted through one of the guide holes 114 of the aiming jig 100.

Figures 7A, 7B:
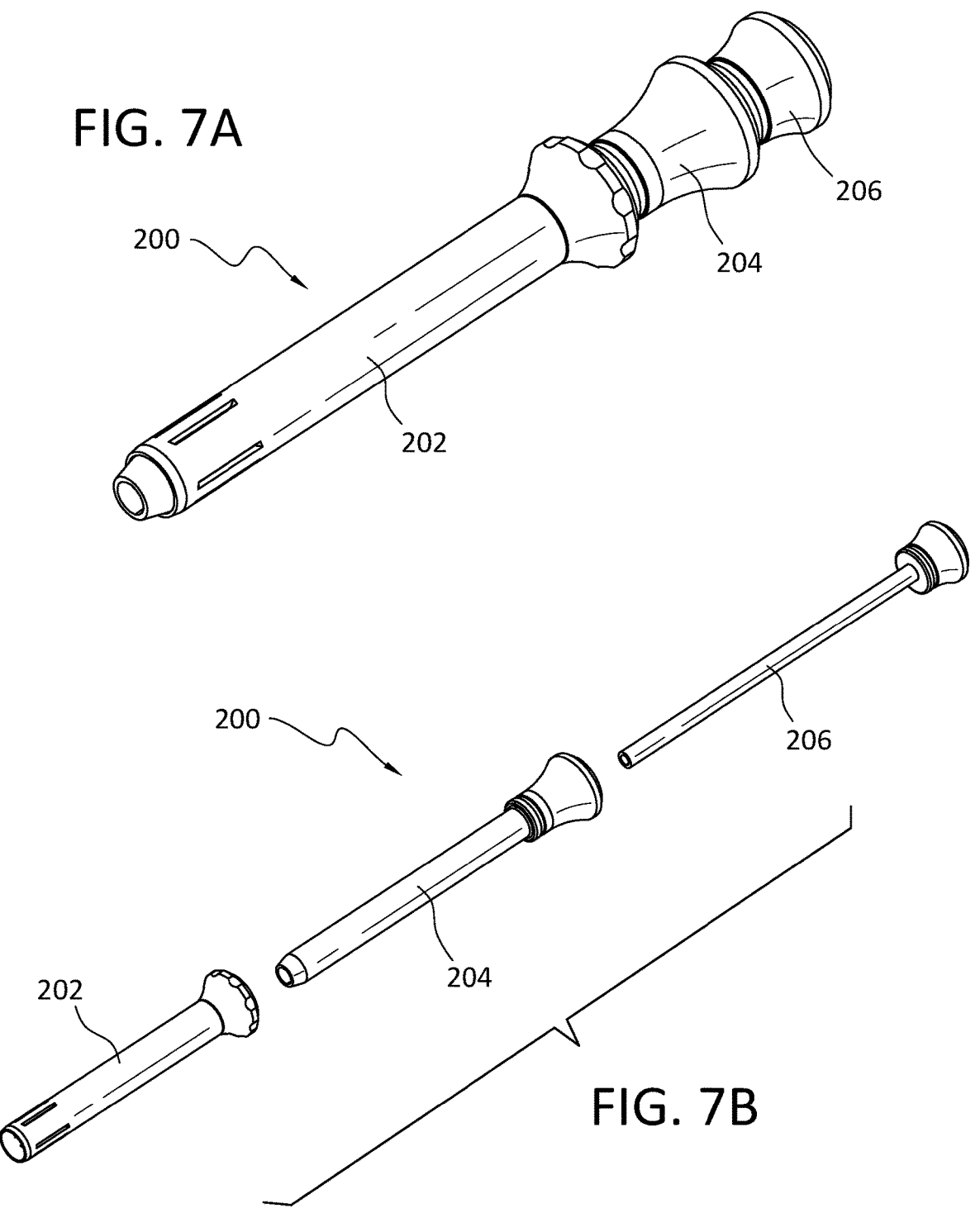
FIGS. 7A-B illustrate a perspective and expanded view of one configuration of the triple sleeve system.

FIGS. 7A-B illustrate a perspective and expanded view of one configuration of the triple sleeve system 200. In FIGS. 7A-B the outer sleeve 202, middle sleeve 204, and inner sleeve 206 are illustrated. Each of these sleeves have different inner diameters that allow for different diameter items to be inserted therethrough. For example, a K-wire may be inserted through inner sleeve 206. Then the inner sleeve 206 may be removed, and then a drill bit may be placed through the middle sleeve 204 to drill a hole in the tibia 2. Next, the middle sleeve 204 is removed, and a screw is inserted through the outer sleeve 202 to be placed in the tibia 2. The triple sleeve system 200 may be used in other ways as well. For example, it may be sued with screw holes 108.

Figure 7C:
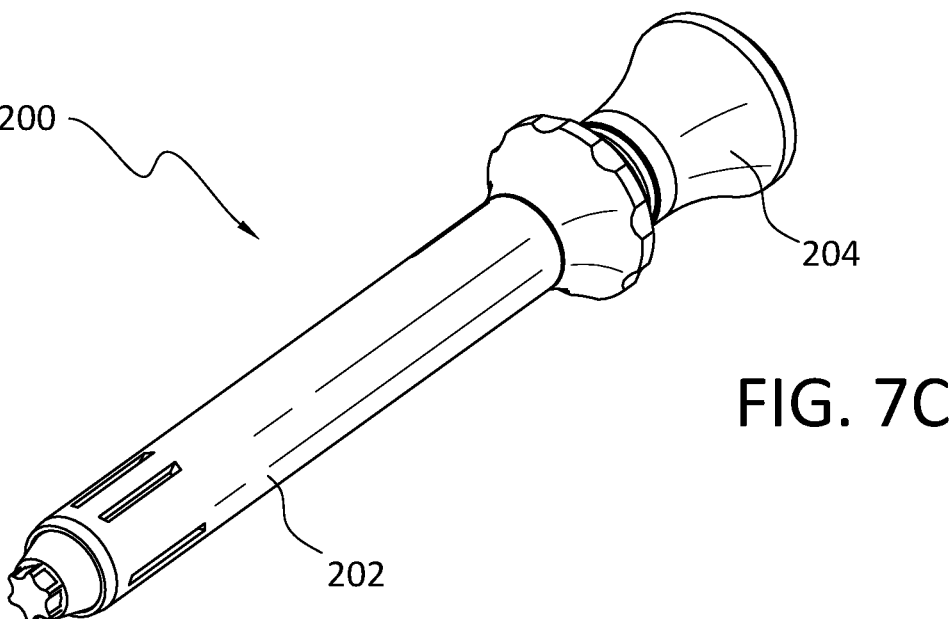
FIGS. 7C-D illustrate a perspective and expanded view of another configuration of the triple sleeve system.
Figure 7D:
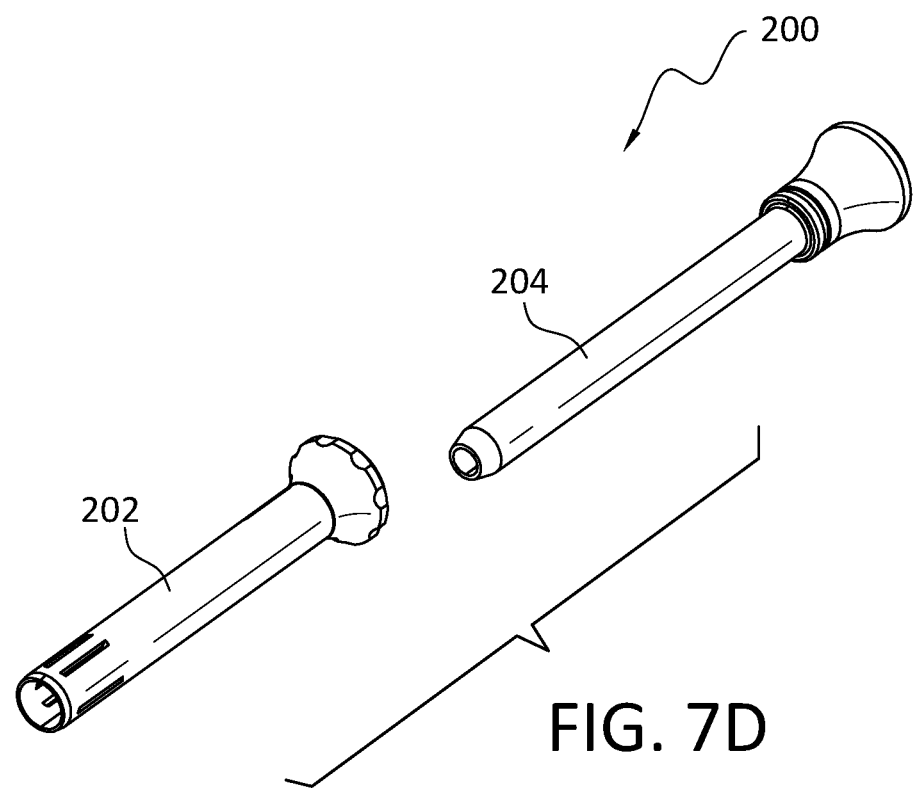

FIGS. 7C-D illustrate a perspective and expanded view of another configuration of the triple sleeve system 200. In In FIGS. 7C-D the outer sleeve 202, and middle sleeve 204 are illustrated. A driver (not shown) may be used to drive a screw into the tibia 2. The guide hole 114 may be used to guide other instruments and tools using other guide systems. The guide holes 114 are oriented so that the "support screws" may be placed without interfering with the raft screws that are placed through the tibia plate 6. Further, these support screws do not extend through and exit the tibia.

A method of using the aiming jig 100 with a tibia plate 6 will now be described. First the surgeon opens the area of the patient near the knee where the tibia plate 6 will be placed. The tibia plate 6 is then placed on the tibia 2 of the patient. This may be done by sliding the body of the tibia plate 6 into the surgical opening down along the shaft of the tibia 2. The surgeon then positions and holds the tibia plate 6 in the desired position relative to the tibia 2. Then the tibia plate 6 may be initially fixed on the tibia 2 using for example one or more K-wires. The K-wires may be driven through the plate fixation holes 14 to provide an initial position of the tibia plate 6 on the tibia 2. At this point one or more plate screws 8 may be placed into the tibia 2 through plate screw holes 10 to secure the tibia 2. In this case the K-wires may be removed. In another embodiment, the plate screws 8 are not yet placed and the K-wires remain in place to temporarily fix the tibia plate 6 to the tibia 2. Next the surgeon may place the aiming jig 100 onto the tibia 2. If K-wires remain in place, then the aiming jig 100 is placed over the K-wires using the proper guide holes 114 corresponding to the plate fixation holes 14 with the K-wires. If the K-wires are not present, then the aiming jig 100 is simply placed over the head of the tibia plate 6. The fixation protrusion 120 are aligned with and inserted into the fixation openings 16. This ensures that the aiming jig 100 is properly aligned with the tibia plate 6. Next a fixation screw 12 may engage the fixation screw hole 116 to fix the aiming jig 100 to the tibia plate 6. In an alternative embodiment, the aiming jig 100 may be placed on the tibia plate 6 before the tibia plate 6 is temporarily fixed to the patient. In this case, the aiming jig 100 may be used to help in sliding the tibia plate 6 along the tibia 4. Then the K-wires may be used for temporarily attaching the tibia plate 6 to the tibia 4. Next, the surgeon places plate screws 8 in the upper most plate screw holes 10 on the tibia plate 6 that are adjacent the articular surface of the tibia 2 if these screws were not previously placed as part of the initial securing of the tibia plate 6 to the tibia 2. These are the raft screws described above. The aiming jig 100 may serve as a guide for the drilling and placement of these plate screws 8. This placement of these screws includes inserting a K-wire, drilling a hole in the tibia 2 and then driving the screw into the hole in the tibia 2. The aiming jig 100 may be used with the triple sleeve system 200 to guide the drilling of the hole and the driving of the plate screw 8 or another drill guide may be used. Also the triple sleeve system 200 or a screw driving guide may be used to assist in properly orienting the screw when it is driven into the tibia 2. Next, the surgeon may drive one or more support screws into the tibia 2 using the guide 112 of the aiming jig 100 in a generally anterior to posterior direction. This may be accomplished using the triple sleeve system 200. The outer sleeve 202 may be inserted through one of the guide holes 114 and placed into contact with the skin of the patient to determine the location for an incision in the skin that reaches to the cortex of the tibia 2. This incision may be a minimally invasive surgery (MIS) incision. The surgeon then makes the MIS incision to expose the cortex of the tibia 2. The triple sleeve system 200 may then be used to drive a K-wire into the bone, drill a hole in the tibia 2, and to drive a support screw into the hole drilled in the tibia 2. The surgeon may then place any additional support screws as needed. Then the surgeon may place any other screws needed to secure the tibia plate 6 to the tibia 2 and to capture bone fragments and to reduce the fracture. The surgeon may remove the aiming jig 100 from the tibia plate 6. The aiming jig 100 may be removed from the tibia plate 6 by disengaging the fixation screw 12 from the plate fixation hole 116 and then lifting the aiming jig 100 off of the tibia plate 6. The surgeon may then complete the surgery by closing the various incisions and carrying out any other normal surgical steps. It is noted that the precise order of the above steps may be varied, especially those relating to the temporary fixation of the tibia plate 6 to the tibia 2, the placement of the plate screws 8, and the placement and removal of the aiming jig 100 from the tibia plate 6.

The foregoing disclosure provides illustration and description but is not intended to be exhaustive or to limit the aspects to the precise form disclosed. Modifications and variations may be made in light of the above disclosure or may be acquired from practice of the aspects.

As used herein, the term "component" is intended to be broadly construed as hardware, firmware, and/or a combination of hardware and software. As used herein, a processor is implemented in hardware, firmware, and/or a combination of hardware and software.

Unless stated otherwise, terms such as "first" and "second" are used to arbitrarily distinguish between the elements such terms describe. Thus, these terms are not necessarily intended to indicate temporal or other prioritization of such elements.

It should be appreciated by those skilled in the art that any block diagrams herein represent conceptual views of illustrative hardware embodying the principles of the aspects.

While each of the embodiments are described above in terms of their structural arrangements, it should be appreciated that the aspects also cover the associated methods of using the embodiments described above.

Even though particular combinations of features are recited in the claims and/or disclosed in the specification, these combinations are not intended to limit the disclosure of various aspects. In fact, many of these features may be combined in ways not specifically recited in the claims and/or disclosed in the specification. Although each dependent claim listed below may directly depend on only one claim, the disclosure of various aspects includes each dependent claim in combination with every other claim in the claim set. A phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Furthermore, as used herein, the terms "set" and "group" are intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," and/or the like are intended to be open-ended terms. Further, the phrase "based on" is intended to mean "based, at least in part, on" unless explicitly stated otherwise.

The invention claimed is:

1. A system comprising an aiming jig and a tibia plate,
wherein the tibia plate has a first head with a fixation opening and a plurality of screw holes through the first head; and
wherein the aiming jig comprises:
   a second head, the second head being configured to interface with the first head, wherein the first head is configured to follow the contours of a tibial condyle;
   a plurality of screw guide holes in the second head corresponding to the plurality of screw holes through the first head;
   a fixation protrusion configured to engage the fixation opening in the first head, wherein an engagement of the fixation protrusion with the fixation opening aligns the second head with the first head; and
   an arm extending from the second head including a guide, wherein the guide is configured to extend along an anterior portion of a tibia when the aiming jig is fixed to the tibia plate, and
   the guide includes a support screw guide hole configured to guide a placement of a support screw into the tibia in a generally anterior to posterior direction so that the support screw avoids interfering with plate screws placed in the first head.

2. The system of claim 1, wherein the tibia plate further comprises a plurality of plate guide holes, and the second head further comprises a plurality of guide holes corresponding to the plurality of plate guide holes in the tibia plate.

3. The system of claim 1, wherein the arm is configured so that the guide avoids contact with a patient when the aiming jig is fixed to the tibia plate.

4. The system of claim 1, wherein the guide includes a plurality of guide holes.

5. The system of claim 1, further comprising a sleeve configured to be inserted in the support screw guide hole and to come into contact with an anterior surface of the tibia.

6. The system of claim 1, further comprising a retention pin configured to be inserted into a retention opening in the guide wherein the retention pin retains the sleeve and fixes the sleeve to the guide.

7. The system of claim 1, wherein the support screw guide hole has a location and orientation so that the support screw is placed between the plate screws and an articular surface of the tibia.

8. The system of claim 1, wherein the support screw guide hole has a location and orientation so that the support screw is placed so that a portion of the plate screws are between the support screw and an articular surface of the tibia.

9. The system of claim 1, wherein the support screw guide hole is configured to guide an end of the support screw to a position within the tibia.

10. The system of claim 1, wherein;

the tibia plate includes a fixation opening;

the second head includes a fixation screw hole, and the aiming jig includes a fixation screw configured to engage the fixation opening in the tibia plate via the fixation screw hole.

11. The system of claim 1, wherein the second head includes a body with a first portion of the plurality of screw guide holes configured to guide a first portion of the plate screws placed in the first head of the tibia plate to support an articular surface of the tibia.

12. The system of claim 11, wherein the second head includes a flange extending from the body with a second portion of the plurality of screw guide holes configured to guide a second portion of the plate screws placed in the first head of the tibia plate, and wherein the flange includes a fixation screw hole configured to receive a fixation screw wherein the fixation screw is configured to engage a fixation opening in the tibia plate via the fixation screw hole.

13. A method for placing support screws into an anterior surface of a tibia using an aiming jig for a tibia plate, comprising:

placing and aligning the tibia plate on the tibia;

initially fixing the tibia plate to the tibia;

placing the aiming jig onto the tibia plate; and placing a support screw in a generally anterior to posterior direction of the tibia using a guide on the aiming jig so that the support screw avoids interfering with plate screws placed in a head of the tibia plate.

14. The method of claim 13, wherein initially fixing the tibia plate to the tibia includes placing plate screws in the tibia plate using guide holes in the aiming jig.

15. The method of claim 13, wherein initially fixing the tibia plate to the tibia includes placing K-wires into the tibia through a guide hole in the aiming jig and a plate fixation hole in the tibia plate.

16. The method of claim 13, wherein placing and aligning the tibia plate on the tibia includes placing a fixation protrusion on the aiming jig into a fixation opening in the tibia plate.

17. The method of claim 13, wherein placing a support screw includes:

drilling a hole in an anterior surface of the tibia using the guide; and driving the support screw into the drilled hole using the guide.

18. The method of claim 17, wherein drilling the hole includes using a first sleeve in the guide, and driving the support screw includes using a second sleeve in the guide.

19. The method of claim 18, further comprising retaining the first sleeve by the guide using a retention pin in the guide.

20. The method of claim 17, wherein placing a support screw includes cutting a minimally invasive surgery incision through soft tissue to expose a cortex of an anterior surface of the tibia.

21. The method of claim 13, wherein the aiming jig comprises:

a head configured interface with a head of the tibia plate comprising:

a plurality of screw guide holes corresponding to a plurality of screw holes in the head of the tibia plate;

a fixation protrusion configured to engage a fixation opening in the head of the tibia plate, wherein an engagement of the fixation protrusion with the fixation opening aligns the head with the head of the tibia plate; and an arm extending from the head including a guide wherein the guide extends along an anterior portion of the tibia when the aiming jig is fixed to the tibia plate, and the guide includes a support screw guide hole configured to guide a placement of a support screw into the tibia in a generally anterior to posterior direction so that the support screw avoids interfering with plate screws placed in the head of the tibia plate.

* * * * *